United States Patent [19]

Dodin et al.

[11] Patent Number: 4,751,053
[45] Date of Patent: Jun. 14, 1988

[54] MAGNETIC DEVICE FOR REMOVING MAGNETIC GEL BALLS FROM A MEDIUM TO BE ANALYZED AND TRANSFERRING THEM TO AN IMMUNOENZYMATIC QUANTITATIVE ANAYLSIS MEDIUM

[75] Inventors: André Dodin, Milly-La-Foret; Bernard Muller, St. Germain en Laye, both of France

[73] Assignee: Institut Pasteur, Paris, France

[21] Appl. No.: 790,100

[22] Filed: Oct. 22, 1985

[30] Foreign Application Priority Data

Oct. 23, 1984 [FR] France ................................ 84 16170

[51] Int. Cl.⁴ .............................................. G01N 1/18
[52] U.S. Cl. ...................................... 422/101; 422/99; 436/177; 436/178; 436/526; 210/222
[58] Field of Search ........................... 422/99, 101, 49; 436/177, 178, 526; 210/222; 294/65.5; 285/348; 435/287

[56] References Cited

U.S. PATENT DOCUMENTS

| | | | |
|---|---|---|---|
| 1,558,447 | 10/1925 | Beach | 335/293 |
| 1,904,224 | 4/1933 | Hargrove | 294/65.5 |
| 2,163,810 | 6/1939 | Raybould | 285/348 |
| 2,471,764 | 5/1949 | Miller | 294/65.5 |
| 2,735,700 | 2/1956 | Bowan et al. | 285/348 |
| 2,816,743 | 12/1957 | Kirkland | 422/99 |
| 3,011,819 | 12/1961 | Moseley, Jr. | 294/65.5 |
| 3,985,649 | 10/1976 | Eddelman | 436/177 |
| 4,272,510 | 6/1981 | Smith | 436/804 |
| 4,512,790 | 4/1985 | Faure et al. | 285/348 |
| 4,649,116 | 3/1987 | Daty et al. | 294/65.5 |

FOREIGN PATENT DOCUMENTS 606485 6/1926 France ................................ 335/293
233674 11/1944 Switzerland .

Primary Examiner—Barry S. Richman
Assistant Examiner—Lynn Kummert
Attorney, Agent, or Firm—Bell, Seltzer, Park & Gibson

[57] ABSTRACT

A magnetic device is provided for removing magnetic gel balls or the like from a liquid to be analyzed, biological or not, and transferring them to an immunoenzymatic quantitative analysis medium, which device is of the type comprising a ferromagnetic material rod, an oblong case made from a non-magnetic material partially enveloping the rod and a circuit for electromagnetically energizing the rod. The device further comprises structure for fixing and centering the rod by clamping.

5 Claims, 1 Drawing Sheet

MAGNETIC DEVICE FOR REMOVING MAGNETIC GEL BALLS FROM A MEDIUM TO BE ANALYZED AND TRANSFERRING THEM TO AN IMMUNOENZYMATIC QUANTITATIVE ANAYLSIS MEDIUM

BACKGROUND OF THE INVENTION

1. Field of the Invention

The present invention relates to a novel magnetic device for removing magnetic gel balls from a liquid medium, biological or not, such as blood, urine, water, milk, effluents, etc. . . . , for performing a diagnosis of pathogenic germs by transferring these balls to an immunoenzymatic quantitative analysis medium.

2. Description of the Prior Art

The U.S. Pat. No. 4,649,116 of the INSTITUT PASTEUR describes a device of the type comprising a magnetized rod, in which the rod is formed from an upper part made from a non-magnetic material fitted, by means of a catch or bayonet system, in a lower part made from a magnetic material.

This rod cooperates with a case of insulating material, formed more especially as an insulating handle, which contains a magnet and is provided over the whole of its height with a through orifice, in particular off centered, for guiding the rod; said rod also cooperates with a spring mounted on this rod between a thrust washer, fixed at the upper end of the rod and the upper face of the case: a pressure exerted on the upper end of the rod causes this latter to slide downwards for removing magnetic gel balls from a medium to be analyzed, whereas release of said pressure causes the rod to return under the action of the spring and allows said magnetic balls to be transferred to an immunoenzymatic quantitative analysis medium so as to substantially reduce, during the transfer operation, any undesirable accidental contact between the magnetized rod and naturally magnetic surfaces, thus implementing the quantitative analysis processes claimed in French Pat. Nos. 2 334 106 and 2 537 725 to the INSTITUT PASTEUR.

SUMMARY OF THE INVENTION

The aim of the present invention is to provide a magnetic device which answers better the requirements of practice than the above mentioned magnetic device provided for the same purpose, more especially in that:

the need for disposing an auxiliary magnet outside the receptacle containing the immunoenzymatic quantitative analysis medium is eliminated, and the device is easier to handle.

The present invention provides then a magnetic device for removing magnetic gel balls or the like from a liquid medium to be analyzed, biological or not, and transferring them to an immunoenzymatic quantitative analysis medium, which device is of the type comprising:

a case formed from a non-magnetic material, a rod formed from a ferromagnetic material, said rod having one end portion positioned within said case and the opposite end portion projecting from the case, clamping means cooperating with said rod for clamping said rod in position in said case, and making it detachable from the case, said clamping means comprising a deformable sleeve and a rigid sleeve serially disposed about said rod with an end of said rigid sleeve abutting an end of said deformable sleeve, and detachable means for compressing said rigid sleeve against the deformable sleeve so that deformation of the deformable sleeve causes clamping of said rod and fixing and centering thereof with respect to said case, a circuit for electromagnetically energizing said rod, said circuit comprising an electric winding housed in said case and wound about said rod and operable for generating an electromagnetic field about said rod upon energization of the winding, an electric cell in said case for energizing said winding, a manually actuable control switch, and means electrically connecting said electric winding, said electric cell and said control switch in series so that, upon actuation of the control switch, the electric winding is energized and the projecting end portion of said rod is magnetized.

In an advantageous arrangement of this embodiment, a housing for the deformable and rigid sleeves is formed by a sleeve coaxial with the case and integrally molded therewith, which housing sleeve projects outwardly and downwardly from the closure base of the case which is pierced with a central orifice for passing the rod therethrough, said means for compressing the rigid sleeve against the deformable sleeve being formed by a plastic material ring screwed about the housing sleeve.

In another advantageous embodiment of the device of the invention, the power supply cell is housed in the case, where it is disposed above the energization winding, which is in the form of a solenoid and rests on the closure base of the case, and said case comprises a closure cap, also made from a non-magnetic material, which is screwed about the upper end of the case and which is provided with a central orifice for fitting the switch controlling the energization circuit formed by a control contactor switch.

In another advantageous arrangement of this embodiment, the energization solenoid is wound directly on the soft iron rod.

In a preferred variant of this arrangement, the energization solenoid is wound about the rod via a solid support, more especially formed by a non-magnetic material sleeve, which is slightly force fitted about the rod.

In another advantageous embodiment of the device of the invention, the rod is removable and sterilisable.

In another advantageous embodiment of the device of the invention, the rod is interchangeable as a function of its diameter.

In a preferred arrangement of this embodiment the rod comprises an upper portion of constant diameter, intended to be enveloped by said solenoid and said housing sleeve, and a lower portion of variable diameter as a substantially inverse function of the foreseeable concentration of pathogenic germs in the medium to be analyzed.

Besides the preceding arrangements, the invention comprises other arrangements which will be clear from the following description.

BRIEF DESCRIPTION OF THE DRAWINGS

The invention will be better understood from the complement of description which follows with reference to the accompanying drawings in which.

It should of course be understood, however, that these drawings and the corresponding descriptive parts are given solely by way of illustration of the subject of the invention of which they in no way form a limitation.

DESCRIPTION OF THE PREFERRED EMBODIMENT

Figure 1:
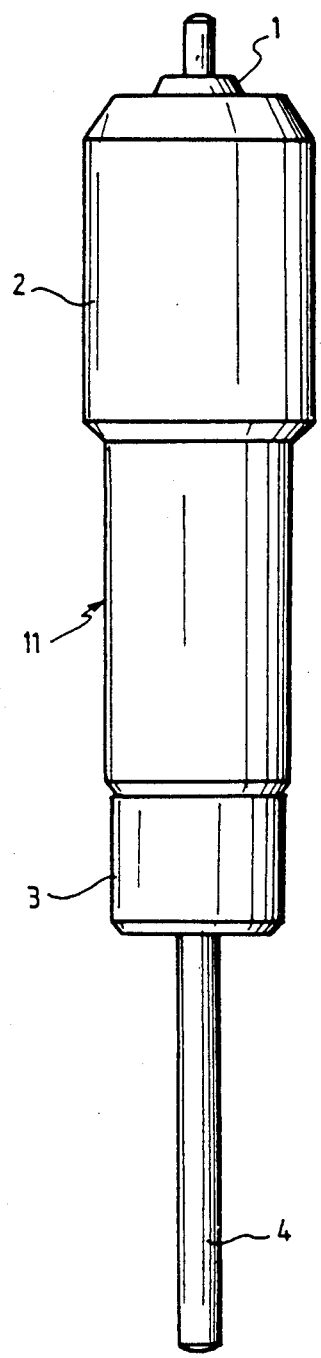
FIG. 1 is a general view in elevation of the magnetic device in accordance with the present invention.

FIG. 1 shows the magnetic device of the invention in the rest position, namely with the control contactor 1 not depressed or open.

From top to bottom there can be seen besides said contactor 1, a cap 2 to which this latter is fixed and which envelops the upper end of an oblong, preferably cylindrical, case 11 and a ring 3 at the lower part of case 11; this latter, as well as cap 2 and ring 3 are made from an insulating material, more especially a plastic material. A metal rod 4, made more especially from soft iron, projects downwardly from the center of ring 3.

Figure 2:
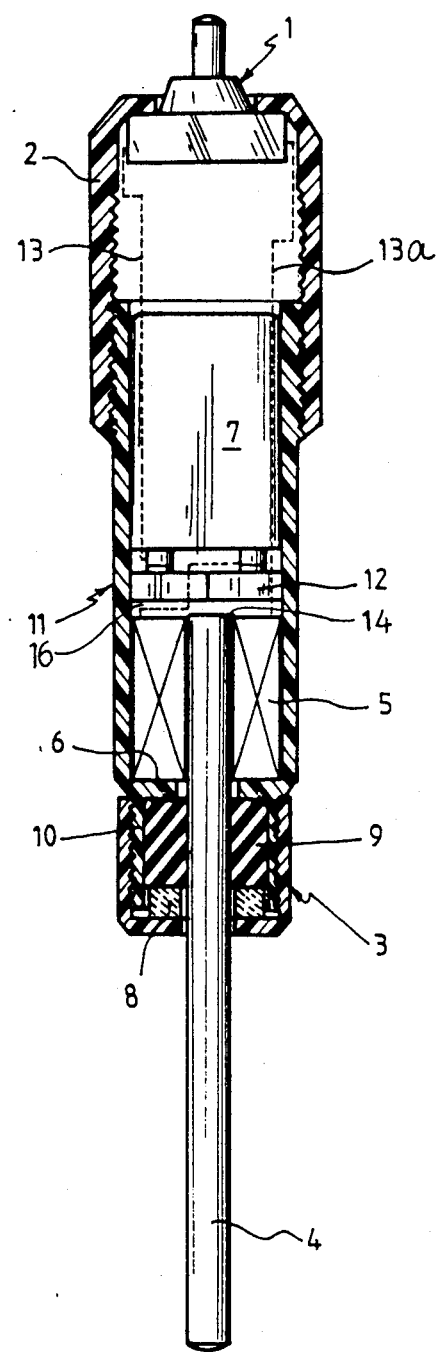
FIG. 2 is a longitudinal sectional view of the device shown in FIG. 1.

FIG. 2 shows the mutual relations of the different elements which form the device of the invention, when they are assembled together.

In particular, the following components of the circuit for electromagnetically energizing rod 4 can be seen, namely:

an energization solenoid 5 which is formed with an appropriate number of turns (about 350 turns of enamelled wire of a diameter equal to 0.5 mm in the example shown) and which is disposed inside said case 11 so as to bear against the closure base 6 of this case, and an electric cell 7 for supplying the electromagnetic energization circuit with DC current, which is in particular of the rechargeable type and which is disposed above the solenoid 5; the cell is separated therefrom by a clip device 12. One terminal of the clip device 12 is connected by wire 13 to a terminal of contactor 1, while the other terminal of clip device 12 is connected by wire 16 to the solenoid 5. The other terminal of contactor 1 is connected by wire 13a to the remaining terminal of the solenoid. Thus, cell 7, contactor 1 and solenoid 5 are in series with each other and form the electric part of the electromagnetic energization circuit of rod 4 (in the example in question, a 9 volt cell is used).

The magnetic part (or core) of this electromagnetic energization circuit is formed by the same soft iron rod 4, about which solenoid 5 is wound. This rod passes through an orifice formed in ring 3, as well as through a "teflon" (PTFE) washer 8 and through a rubber seal 9 housed inside a sleeve 10: it is advantageous for the height of solenoid 5 to be at the minimum equal to ¼ of the length of rod 4, which, in the example shown is 130 mm.

Solenoid 5 may be either directly wound on the soft iron rod 4, but in this case the rod cannot be sterilized in an autoclave sterilizer or placed in contact with a disinfectant liquid, or preferably said solenoid may be wound on a solid support, for example formed by a sleeve 14, and in this case the iron rod, since it is no longer fixed to the support of the solenoid, may be sterilized because of its mobility.

This sleeve, which is coaxial with case 11, projects downwardly from the closure base 6 of this case and is provided on its outer surface with a threaded portion for screwing on said ring 3: since before screwing said washer 8 extends slightly externally of sleeve 10, the compression of this washer 8 against seal 9 during screwing up is transmitted to this latter which, by radial dilatation, is capable of clamping rod 4 and holding it in position while providing the required seal with respect to the medium to be analyzed, to the quantitative analysis medium and to the rinsing liquid. In fact, after each use of the device of the invention, the rod is rinsed with physiologically sterile water, followed by dipping in alcohol and flaming: the protection of the rubber seal 9 with respect to the heat released by the flame is provided by a "Teflon" washer 8.

The system for holding rod 4 in position, such as it has just been described, is particularly advantageous when the rod is removable, because—let us repeat it—this arrangement thereof in an autoclave sterilizer, more especially before the first use of the rod (when working with the same medium, it is generally sufficient to pass the rod through a flame, after rinsing and dipping in alcohol).

A second advantage linked to the fact that the rod is made removable, is formed by the possibility of also making it interchangeable, more especially as a function of its diameter. For this, it should be noted that for media to be analyzed having low pathogenic germ concentrations, the preferred diameter of rod 4 is equal to 8 mm, whereas for medium and high concentrations, it is preferable to use rods whose diameters are equal to 5 and 3 mm, respectively.

Thus, so as not to be forced to change more especially both the solenoid and the seal clamping the rod, for adapting their through-orifices to each of the preferred diameter values indicated above for said rod, it is advantageous for rod 4 to comprise an upper portion corresponding, in particular, to the largest diameter and intended to be enveloped by said solenoid and said sleeve 10, and a lower portion (not shown) corresponding substantially to the part which projects from the clamping ring 8, whose diameter is variable as a reverse function of the foreseeable concentration of pathogenic germs, following the considerations previously mentioned. It goes without saying that, when it is not possible to anticipate in which range of values (high, medium or low) is located the order of size of the concentrations of the media to be analyzed, the use of the largest diameter rod is adapted to each case.

The operation of the magnetic ball removal device of the present invention is simple: a pressure exerted on said control contactor switch, in particular by the thumb of the operator, energizes the electromagnetic circuit of which the sampling rod forms a part, whereas release of this contactor cancels out the magnetic field initially maintained by flow of the electric current through the solenoid.

In its application to the immunoenzymatic quantitative analysis processes which form the subject of French Pat. Nos. 2334 106 and 2 537 725, the sampling device in accordance with the invention is placed above a container containing an incubation medium which comprises a liquid medium, biological or not, and magnetic gel balls coupled to an appropriate protein for performing the immunoenzymatic quantitative analysis: it is sufficient to introduce the tip of the sample rod, while pressing the contactor, and to transfer the magnetic gel balls which have been attracted by the rod and which are attached to the tip thereof, to the surface of an appropriate immunoenzymatic quantitative analysis medium contained in another container, by releasing the control contactor: thus, a part at least of the balls taken separates by adherence to the quantitative analysis medium, so that no auxiliary magnet is necessary (it should be recalled that with the sampling device described in U.S. Pat. No. 4,649,116, because of the high residual magnetization induced by the permanent sampling magnet in the lower magnetic part of the rod, a permanent magnet must be used which is more powerful than the sampling magnet and which is disposed externally of the container containing the quantitative analysis medium, for separating the magnetic gel balls taken from the rod which carries them).

After placing the magnetic balls on the quantitative analysis medium, the rod is rinsed with physiologically sterile water, and then dipped in alcohol and passed through a flame—as mentioned above—so that the device of the invention is ready for a new operation.

As is clear from the foregoing, the invention is not limited to those of its modes of application and embodiments which have been described more explicitly; it embraces, on the contrary, all variants thereof which may occur to a technician skilled in the technique, without departing from the scope or spirit of the present invention.

What is claimed is:

1. A magnetic device for removing magnetic gel balls or the like from a liquid medium to be analyzed and for transferring such balls to an immunoenzymatic quantitative analysis medium, said device comprising:
   a case formed from a non-magnetic material,
   a rod formed from a ferromagnetic material, said rod having one end portion positioned within said case and an opposite end portion projecting from the case;
   clamping means cooperating with said rod for detachably clamping said rod in position in said case, said clamping means comprising a deformable sleeve and a rigid sleeve serially disposed about said rod with an end of said deformable sleeve abutting an end of said rigid sleeve, and detachable means for compressing said rigid sleeve against the deformable sleeve so that deformation of the deformable sleeve causes clamping of said rod and fixing and centering thereof with respect to said case;
   a circuit for electromagnetically energizing said rod, said circuit comprising
   an electric winding housed in said case and wound about said rod and operable for generating an electromagnetic field about said rod upon energization of the winding,
   an electric cell in said case positioned and arranged for energizing said winding,
   a manually actuatable control switch carried by said case, and
   means electrically connecting said electric winding, said electric cell and said control switch in series so that, upon actuation of the control switch, the electric winding is energized and said opposite end portion of said rod is magnetized.

2. The device as claimed in claim 1, including a housing for said deformable and rigid sleeves, said housing comprising an externally threaded cylindrical collar disposed coaxially with said case and integrally molded therewith, said collar extending from a centrally apertured closure of one end portion of said case separating said one end portion of said rod from said opposite end portion of the same, and wherein said detachable means for compressing said rigid sleeve against said deformable sleeve comprises an internally threaded centrally apertured closure cap disposed about said rod and threadably secured to said externally threaded housing collar and constructed and arranged to compress said rigid and deformable sleeves against said apertured closure of said one end portion of the case.

3. The device as claimed in claim 1, wherein said case includes a closure cap, also formed from a non-magnetic material, and which is screwed about the end portion of the case opposite to said one end portion of the case, said cap having a central opening for receiving said control switch.

4. The device as claimed in claim 1, wherein said winding is wound about said one end portion of the rod and said one end portion of said rod is of a predetermined constant diameter, and wherein said opposite end portion of the rod which projects from the case is of a different diameter.

5. A magnetic device for removing magnetic gel balls or the like from a liquid medium to be analyzed and for transferring such balls to an immunoenzymatic quantitative analysis medium, said device comprising:
   an elongate, generally cylindrical hollow case formed from a non-magnetic plastic material;
   an elongate cylindrical rod formed from a ferromagnetic material, said rod being positioned coaxially with said cylindrical case with one end portion thereof located within the case and an opposite end portion projecting axially from one end of the case, said one end of said case having a centrally apertured end closure through which said rod extends, with said end closure separating said one end portion of said rod from said other end portion of said rod;
   an externally threaded cylindrical collar formed integrally with said case at said one end portion of said case, a deformable sleeve and a rigid sleeve serially disposed about said rod with an end of said deformable sleeve abutting an end of said rigid sleeve and positioned within said externally threaded collar, an internally threaded, centrally apertured closure cap threadably secured to said externally threaded collar and said end closure and said closure cap being constructed and arranged for compressing said rigid sleeve against the deformable sleeve so that deformation of the deformable sleeve causes clamping of said rod and fixing and centering thereof with respect to said case;
   a circuit for electromagnetically energizing said rod, said circuit comprising
   an electric winding housed in said case and wound about said one end portion of said road and operable for generating an electromagnetic field about said rod upon energization of the winding,
   an electric cell in said case positioned and arranged for energizing said winding,
   a manually actuatable control switch carried by said case at an end opposite said apertured end closure, and
   means electrically connecting said electric winding, said electric cell and said control switch in series so that, upon actuation of the control switch, the electric winding is energized and said opposite end portion of said rod is magnetized.

* * * * *